US010472291B2

(12) United States Patent
Lewis et al.

(10) Patent No.: US 10,472,291 B2
(45) Date of Patent: Nov. 12, 2019

(54) CROSSLINKED STARCHES FOR PORE FORMING IN CERAMICS

(71) Applicant: Corning Incorporated, Corning, NY (US)

(72) Inventors: Mark Alan Lewis, Horseheads, NY (US); Pascale Oram, Painted Post, NY (US); Cameron Wayne Tanner, Horseheads, NY (US); Elizabeth Marie Vileno, Corning, NY (US)

(73) Assignee: Corning Incorporated, Corning, NY (US)

( * ) Notice: Subject to any disclaimer, the term of this patent is extended or adjusted under 35 U.S.C. 154(b) by 325 days.

(21) Appl. No.: 14/484,509

(22) Filed: Sep. 12, 2014

(65) Prior Publication Data
US 2015/0102516 A1 Apr. 16, 2015

Related U.S. Application Data (60) Provisional application No. 61/891,079, filed on Oct. 15, 2013.

(51) Int. Cl.
*C04B 38/00* (2006.01)
*B28B 3/20* (2006.01)
(Continued)

(52) U.S. Cl.
CPC ............ *C04B 38/0087* (2013.01); *B28B 3/20* (2013.01); *C04B 35/185* (2013.01);
(Continued)

(58) Field of Classification Search
CPC . C04B 38/00; C04B 38/0006; C04B 38/0074; C04B 38/06
See application file for complete search history.

(56) References Cited

U.S. PATENT DOCUMENTS 6,620,751 B1 * 9/2003 Ogunwumi ........... C04B 35/478
501/128
7,141,089 B2 11/2006 Beall et al.
(Continued)

FOREIGN PATENT DOCUMENTS

| GB | 999983 A | 7/1965 |
| JP | 53085850 A | 7/1978 |
| WO | 2012074944 A1 | 6/2012 |

OTHER PUBLICATIONS

Mar. 5, 2015 International Search Report issued in counterpart application No. PCTUS2014/060641.
(Continued)

*Primary Examiner* — Erin Snelting
(74) *Attorney, Agent, or Firm* — Kurt R. Denniston (57) ABSTRACT

Disclosed herein are green bodies comprising at least one ceramic-forming powder; at least one binder; and at least one cross-linked starch present in an amount of at least about 20% by weight as a super addition. Further disclosed herein is a method of making a porous ceramic body comprising mixing at least one ceramic-forming powder, at least one solvent such as water, at least one binder, and at least one cross-linked starch present in an amount of about 20% by weight as a super addition to form a batch composition; extruding the batch composition to form a green body; drying the green body; and firing the green body to form a porous ceramic body. Also disclosed herein are methods of screening a green body for making a porous ceramic body.

8 Claims, 4 Drawing Sheets (51) Int. Cl.
| | |
|---|---|
| C04B 35/64 | (2006.01) |
| C04B 35/478 | (2006.01) |
| C04B 35/636 | (2006.01) |
| C04B 35/638 | (2006.01) |
| C04B 38/06 | (2006.01) |
| C04B 103/42 | (2006.01) |
| C04B 35/185 | (2006.01) |
| C04B 35/195 | (2006.01) |
| G01N 33/38 | (2006.01) |
| G01N 33/00 | (2006.01) |
| C04B 111/32 | (2006.01) |
| C04B 111/00 | (2006.01) |

(52) U.S. Cl.
CPC .......... *C04B 35/195* (2013.01); *C04B 35/478* (2013.01); *C04B 35/636* (2013.01); *C04B 35/638* (2013.01); *C04B 35/64* (2013.01); *C04B 38/00* (2013.01); *C04B 38/0006* (2013.01); *C04B 38/0067* (2013.01); *C04B 38/06* (2013.01); *C04B 38/0645* (2013.01); *G01N 33/388* (2013.01); *C04B 2103/42* (2013.01); *C04B 2111/0081* (2013.01); *C04B 2111/00793* (2013.01); *C04B 2111/32* (2013.01); *C04B 2235/606* (2013.01); *G01N 2033/0091* (2013.01)

(56) References Cited

U.S. PATENT DOCUMENTS

| | | | | |
|---|---|---|---|---|
| 7,208,108 | B2 | 4/2007 | Otsuka et al. | 264/44 |
| 7,575,618 | B2 | 8/2009 | Miao et al. | 55/523 |
| 7,744,670 | B2 | 6/2010 | Miao et al. | 55/523 |
| 7,887,897 | B2 | 2/2011 | Lu et al. | 428/116 |
| 8,097,203 | B2 | 1/2012 | Miao et al. | |
| 8,138,108 | B2 | 3/2012 | Tepesch et al. | 501/80 |
| 8,394,167 | B2 | 3/2013 | Merkel et al. | 55/523 |
| 8,673,045 | B2 | 3/2014 | Merkel et al. | 55/523 |
| 2004/0051196 | A1 | 3/2004 | Otsuka et al. | 264/41 |
| 2005/0069469 | A1 | 3/2005 | Fu et al. | |
| 2006/0021308 | A1 | 2/2006 | Merkel et al. | 55/523 |
| 2010/0222200 | A1* | 9/2010 | Tepesch | C04B 35/478 501/83 |
| 2011/0121007 | A1 | 5/2011 | Nottingham et al. | |
| 2011/0212007 | A1 | 9/2011 | Lu et al. | 423/213.5 |
| 2012/0134891 | A1* | 5/2012 | Boger | B01D 46/2425 422/211 |
| 2013/0111862 | A1 | 3/2013 | Divens-Dutcher et al. | 55/523 |

OTHER PUBLICATIONS

Baumann et al. "Manufacturing Strategies for Asymmetric Ceramic Membranes for Efficient Separation of Oxygen from Air," J. European Cer. Soc., 33 (2013). pp. 1251-1261.
Biliadaris, "Structural Transitions and Related Physical Properties of Starch," Chapter 8 in Starch: Chemistry and Technology, Third Edition, ISBN 978-0-12-746275-2, p. 311. (2009).
Farrauto et al. "Reducing truck diesel emissions: a status report", Automotive Engineer, 100 (1992) 19-23.
Hellman et al, "Starch granule swelling in water vapor sorption" JACS, 74 (1952) 348-350.
Honda et al, "Improvement on characteristics of porous alumina from platelets using TEOS treatment," Ceramics International, 39 (2013) 1265-1270.
Kulkarn, "Cellular ceramic products help curb diesel engine emissions" Automotive Engineer, 100 (1992) 21-25.
Lyckefeldt and Ferreira, "Processing of Porous Ceramics by 'Starch Consolidation'," J. Eur. Ceram. Soc., 18 (1998) 131-140.
Reed, Principles of Ceramics Processing, Chapter 7: Drying, Second Edition, published by Wiley-Interscience, New York, New York, ISBN 0-471-59721-X, (1995) pp. 545-561.
Sarikaya and Dogan, "Effect of various pore formers on microstructural development of tape-cast porous ceramics," Ceramics International, 39 (2013) 403-413.
Sheppard, "Porous Cermaics: processing and applications" Porous Materials, Ceramic Transactions 31 (1993) 3-23.
Singhal, "Advances in Tubular Solid Oxide Fuel Cell Technology"; Proceedings of the Fourth International Symposium on Solid Oxide Fuel Cells, edited by M. Dokiya, O. Yamamoto, H. Tagawa, and S.C. Singhal, published by the Electrochemical Society, 95-1 (1995) 195. pp. 28-31.
English Translation of JP2016522780 Office Action dated Oct. 31, 2017, Japan Patent Office.
English Translation of CN201480068535.0 Dispatched Mar. 2, 2018; 8 Pages; Chinese Patent Office.

\* cited by examiner

FIG. 4C 120°C 100%Dry

FIG. 5C 120°C 100%Dry

FIG. 4B 105°C 100%Dry

FIG. 5B 105°C 100%Dry

FIG. 4A 80°C 100%Dry

FIG. 5A 85°C 100%Dry

CROSSLINKED STARCHES FOR PORE FORMING IN CERAMICS

This application claims the benefit of priority under 35 U.S.C. § 119 of U.S. Provisional Application Ser. No. 61/891,079 filed on Oct. 15, 2013 the content of which is relied upon and incorporated herein by reference in its entirety.

DESCRIPTION

Technical Field

The present disclosure relates to green bodies comprising at least one ceramic-forming powder; at least one binder; and at least one cross-linked starch present in an amount of at least about 20% by weight as a super addition. Further disclosed herein is a method of making a porous ceramic body comprising mixing at least one ceramic-forming powder, at least one solvent, at least one binder, and at least one cross-linked starch, present in an amount of about 20% by weight as a super addition, to form a batch composition; extruding the batch composition to form a green body; drying the green body; and firing the green body to form a porous ceramic body. Also disclosed herein are methods of screening a green body for making a porous ceramic body if the green body satisfies at least one given parameter.

Background

Porous ceramic bodies may be used in a variety of applications, including, for example, catalytic converter substrates, diesel particulate filters, electrodes for batteries and fuel cells, microfiltration membranes and bioreactors, and insulating materials.

The porosity of a ceramic body may enable or enhance its functionality. For example, for catalytic converters, a high porosity of the substrate may shorten the time to heat the catalyst to an active temperature to reduce cold-start emissions by reducing the heat capacity. The porous microstructure of a ceramic body may also aid in the uptake and adhesion of catalyst washcoats. With regards to filters, increased porosity and/or pore size may aid in removing particulates from a fluid or gas stream without creating a pressure drop that is too high. If the porosity of a ceramic body is too high, however, the ceramic body may have a reduced strength, and cracking of the ceramic body may result. Therefore, it may be advantageous to have ceramic bodies that are highly porous and yet have maintained strength and/or resistance to cracking.

SUMMARY

Disclosed herein are green bodies comprising at least one ceramic-forming powder; at least one binder; and at least one cross-linked starch present in an amount of at least about 20% by weight as a super addition, wherein the green bodies exhibit a growth at about 35° C. and about 85% humidity of less than about 0.8% at least about 24 hours after drying.

Methods for making porous ceramic bodies are also disclosed herein and comprise mixing at least one ceramic-forming powder, at least one solvent such as water, at least one binder, and at least one cross-linked starch present in an amount of about 20% by weight as a super addition to form a batch composition; extruding the batch composition to form a green body; drying the green body; and firing the green body to form a porous ceramic body. In certain embodiments, the green body exhibits a growth at about 35° C. and about 85% humidity of less than about 0.8% at least about 24 hours after drying and before the firing of the green body.

Further disclosed herein are methods of screening a green body for making a porous ceramic body comprising measuring at least one of the percent shrinkage upon drying of the green body and the growth of the green body at least about 24 hours after drying and selecting a green body for use as a porous ceramic body if the green body satisfies at least one of the following parameters: (i) less than about 5% shrinkage upon drying of the green body; and (ii) less than about 0.8% growth of the green body at least about 24 hours after drying.

Both the foregoing general summary and the following detailed description are exemplary only and are not restrictive of the disclosure. Further features and variations may be provided in addition to those set forth in the description. For instance, the disclosure describes various combinations and subcombinations of the features disclosed in the detailed description. In addition, it will be noted that where steps are disclosed, the steps need not be performed in that order unless explicitly stated.

BRIEF DESCRIPTION OF THE DRAWINGS

In FIG. 3, XL indicates crosslinked.

DESCRIPTION OF EXEMPLARY EMBODIMENTS

Since the introduction of substrates in the 1970s and filters in the 1980s, there has been an increasing demand for higher porosity substrates, such as ceramic bodies, to reduce thermal mass and to facilitate earlier activation of catalysts during engine cold starts. Higher porosity in filters also further reduces pressure drop and accommodates larger amounts of catalysts within the filter wall. Higher porosity, however, may weaken the structure of the ceramic body.

Porosity may be controlled in amount and shape in many ceramic bodies by introducing combustible particles, known as pore formers, to a ceramic batch before forming a ceramic body, such as a honeycomb ceramic body. The pore formers occupy space between particles that become the ceramic, leaving behind a pore after firing. Pore formers may include, for example, starch, graphite, and polymer powders. The amount of porosity and the pore size can be tailored in part by the concentration and particle size of the pore formers, respectively. Within limits, greater batch concentrations of the pore former in the ceramic batch composition may give higher porosity, and smaller size particles of the pore former may give smaller pores.

Combustible pore formers are being designed for use in filters and light-duty substrates to meet ever-tightening emissions regulations around the world. The porosity of certain products may range, for example, from about 50% to about 65%, depending upon the application. The creation of such high porosity may require a high concentration of pore former in the batch composition relative to the components that become the ceramic. Porosity, mean pore diameter, and wall thickness targets may be met by selecting the appropriate pore former or combination of pore formers.

Starch is considered an attractive material for pore forming. Starches are available from plant sources in a wide range of particle sizes, and the particle size distribution from a given species may be naturally narrow. Starches may be produced in large quantities as part of agricultural activities. Starches are also inexpensive compared to other known pore formers, such as polymers and graphite. Starch, however, may undergo dimensional instability during processing of a ceramic body that may limit its usefulness for creating high levels of porosity. Accordingly, increasing the amount of starch to yield a composition with suitably high porosity may require increasing the concentration of starch to an unacceptably high concentration, wherein the physical properties of the green body and its subsequent processing may be adversely affected.

Ceramic forming processes like extrusion or slip casting involve mixing of at least one ceramic-forming powder with a solvent, such as water, and a binder to create a paste or slurry known as a batch composition. After forming, the water is removed, and the green body may be stored for some period of time before firing. The drying and firing process steps may be carefully managed to avoid strains that could cause cracking. Extrusion of ceramic bodies, such as honeycomb ceramic bodies, may comprise mixing of at least one ceramic forming powder, such as talc, clay, alumina, and sand, with a solvent, at least one plasticizer, at least one binder, and optionally at least one pore former to form a batch composition that can be pushed through a die to form a desired shape, yielding a wet green body.

The next step in processing of the batch composition is drying the wet green body. The green body may typically shrink by about 1% to about 5% as water leaves the interstitial spaces between the ceramic precursor particles. Differential shrinkage during drying may be the source of defects such as warpage or other distortions in shape and cracks in the green body. Differential drying may be controlled in several ways. For example, differential drying may be controlled by good mixing of the ceramic precursor, uniform distribution of water during forming, controlling the rate of drying, controlling the humidity during drying, forming of the body with lower water content, and/or including binders to increase strength of the green body.

Controlling shrinkage uniformity within the extruded batch composition may be of importance both for minimizing mechanical strains as well as differential shrinkage (both wet-to-dry and dry-to-fired). Controlling shrinkage optimizes the ability to use the batch composition on the manufacturing line. Shrinkage may be impacted by the choice of batch constituents, such as the ceramic-forming powders, binders and other organic additives, such as surfactants or lubricant agents, in addition to pore formers and water.

Extrusion processes are being developed to produce filters and substrates with porosities of greater than about 50%. Creation of this high level of porosity may be accomplished in part by inclusion of combustible pore formers, including starch. The use of starch as a pore former in water-based extrusions may complicate the drying process because of the starch's interactions with water. Starch is sensitive to water absorption in ambient environmental conditions, inducing potential storage and transportation issues, as well as difficulties with predicting how much water should be added during the extrusion process to meet a given optimum process window and optimize throughput.

As the starch granules interact with water during the extrusion process and drying steps, careful temperature monitoring may become important, as the processing temperature becomes close to or exceeds the starch gelatinization temperature. This problem may become more pronounced for ceramic compositions where the starch content by volume percentage exceeds about 10%. Starch may undergo structural changes in response to temperature, water, and environmental conditions it encounters during processing and storage. For example, the crystalline regions of the starch may become amorphous upon exposure to heat. The starch may undergo swelling and dissolution in water at room temperature. Dissolved components of the starch (e.g., amylose) may precipitate outside of the original starch particles, and the starch may recrystallize (retrogradation) on drying and cooling. Volume changes may be associated with each of these processes. The volume changes may influence shrinkage on drying and may also change pore size. Differential strains from these processes may also induce cracking of green bodies during drying and in storage.

There are numerous examples of green bodies cracking during drying or in storage when the green body comprises starch. As the concentration of starch and other pore formers increases in the green body, the green body may show an increased likelihood of cracking and/or increased severity of cracks. It is possible that cracking may not occur or may not be observed during the initial drying step (e.g., microwaving) of processing the green body, but rather during the drying finishing step, after most of the water has already been removed from the green body. Cracking may be evident in any high porosity filter, including cordierite-based and aluminum titanate-based filters for integrated SCR catalysts. Cracking during drying and/or storage is described in the development of high porosity (such as, for example, about 60% to about 70% porosity) ceramic filters that contain starch pore formers. Therefore, when starch is used as a pore former, its concentration is kept low enough to substantially minimize cracking of the green body; this, consequentially, limits the level of porosity of a ceramic body that can be obtained by using starch as a pore former.

It may be possible to inhibit cracking by limiting the level dryness after the initial drying step, for example to less than about 80%; by storing the dried green body in plastic bags after drying to limit interactions with the environment; and/or by controlling the environment (e.g., humidity)

where the green bodies are stored. These solutions, however, are inconvenient and not well-suited to high volume manufacturing.

Cross-Linked Starches

Disclosed herein is the use of crosslinked starches as pore formers for making porous ceramic bodies. In certain embodiments, at least one crosslinked starch may be present in a batch composition in relatively high concentrations, such as, for example, at least about 20% by weight as a super addition. In certain embodiments, the at least one crosslinked starch may be present in a batch composition in an amount ranging from about 20% to about 40%, such as about 20% to about 35%, about 20% to about 30%, or about 28% to about 32%, by weight as a super addition. As used herein, the term "super addition" refers to adding additional ingredients or materials to a batch composition or formulation in excess of, or in addition to, a 100 weight percent base formulation.

In certain embodiments disclosed herein, the crosslinked starch may be used as a pore former if, after complete drying of the resultant green body, there is total growth of less than about 0.5%, such as, for example, less than about 0.3%, after exposure of the green body to about 35° C. in about 85% relative humidity for at least about 24 hours, such as at least about 1 week.

There are numerous advantages of crosslinked starches over native starches for pore forming. Advantages may stem from the reduced interactions with water that occur during processing or in response to environmental conditions during storage. The reduced interactions with water of crosslinked starches may enable at least one of the following: lower overall shrinkage on drying of the green body; drying of the green body comprising higher concentrations of starch without cracking; longer storage life of the green body without cracking; lower residual stress in the green body before firing, which may lead to a higher yield on firing; creation of ceramic bodies with high levels of porosity that may be unattainable with a native starch; larger mean pore diameter than with native starch of the same particle size distribution; and/or a lower cost process than could be achieved using alternative combustible pore formers, such as synthetic polymers.

The porous ceramic bodies disclosed herein may, in certain embodiments, have a porosity greater than about 45%, such as, for example, greater than about 50%, greater than about 60%, greater than about 65%, or ranging from about 50% to about 65%. As used herein, the term "porosity" refers to the total void space in a body, such as a ceramic body, that can be attributed to the presence of pores, as opposed to void space that is attributable to honeycomb structure or channels. Porosity may be expressed as the ratio of the pore volume to the total volume of a body and may be expressed as a percent.

In addition to porosity, pore size distribution may also be measured. Accordingly, $d_{50}$, which may be measured in micrometers, is the pore diameter at which 50% of the porosity of the ceramic body has been intruded by mercury, as measured on the ceramic body by mercury porosimetry. Likewise, $d_{10}$ and $d_{90}$ are equal to the pore diameter at which 90% by volume and 10% by volume, respectively, of the porosity of the ceramic body has been intruded by mercury. Thus, the values of $d_{10}$, $d_{50}$, and $d_{90}$ are the pore diameters at which about 10%, 50%, and 90%, respectively, of the pores are of a smaller diameter on a pore volume basis. In certain embodiments, the pore size distribution may be measured as $(d_{90}-d_{10})/d_{50}$, wherein lower values imply fewer large pores, and vice versa.

The crosslinked starches disclosed herein may have any degree of crosslinking, ranging from low crosslinking to high crosslinking to very high crosslinking. The degree of crosslinking may be controlled, for example, by the amount of crosslinking agent added to a starch. One of ordinary skill in the art would recognize that adding increasing amounts of at least one crosslinking agent to at least one starch may result in increasingly crosslinked starches. Any crosslinking agent known in the art may be used to form the crosslinked starches and/or to increase the degree to which a starch is crosslinked.

Any crosslinked starch known in the art may be used in accordance with the embodiments disclosed herein. Non-limiting examples of crosslinked starches that may be used in accordance with various embodiments include cross-linked potato starches, amioca starches, pea starches, corn starches, sago starches, and mixtures thereof.

Batch Compositions

It is envisioned that the crosslinked starches disclosed herein may be used with any ceramic-forming powder known in the art, including cordierite-forming powders, mullite-forming powders, and aluminum titanate-forming powders, to form a batch composition. As used herein, the term "powder," for example a ceramic-forming powder, refers to any convenient grain size. Grain size may, in certain embodiments, range from about 50 nm to about 5000 microns, such as about 200 nm to about 5000 microns.

The term "batch composition" is used herein to denote a substantially homogenous mixture comprising at least one inorganic ceramic-forming component. In various exemplary embodiments of the present disclosure, the at least one inorganic ceramic-forming component may be chosen from any component suitable to form a desired ceramic composition, for example, alumina sources, silica sources, titania sources, and magnesia sources. The at least one inorganic ceramic-forming component may, in certain embodiments, be in the form of a reactive powder.

Exemplary sources of alumina include, but are not limited to, materials that, when heated to a sufficiently high temperature, alone or in the presence of other materials, will yield aluminum oxide. Non-limiting examples of suitable alumina sources include alpha-alumina; transition aluminas such as gamma, theta, chi, and rho aluminas; hydrated alumina; gibbsite; corundum; boehmite; pseudoboehmite; aluminum hydroxide; aluminum oxyhydroxide; diaspore; and mixtures thereof.

Exemplary sources of silica include, but are not limited to, non-crystalline silica, such as fused silica and sol-gel silica; crystalline silica, such as zeolite, quartz, and cristobalite; silicone resin; diatomaceous silica; kaolin; talc; and mullite. In other embodiments, the silica source may be chosen from silica-forming sources comprising at least one compound that forms free silica when heated, such as, for example, silicic acid and silicone organometallic compounds.

Examples of titania sources include, but are not limited to, rutile, anatase, and amorphous titania. Sources of magnesium include, but are not limited to, talc, magnesite ($MgCO_3$), and any materials that, when heated to a sufficiently high temperature, alone or in the presence of other materials, will yield magnesium oxide. The batch composition may, in various embodiments, be an aluminum titanate forming composition. In such embodiments, the batch material comprises at least one source of alumina and at least one source of titania.

In addition to the at least one crosslinked starch and at least one ceramic-forming powder, the batch compositions disclosed herein may further comprise at least one binder.

By way of example only, the at least one binder may be chosen from organic binders, such as cellulose-containing components, for example, methylcellulose, hydroxypropyl methylcellulose, methylcellulose derivatives, and combinations thereof. In certain non-limiting embodiments, the binder may be present in the batch composition in an amount ranging from about 1% to about 10% by weight, for example, from about 2% to about 6%, or about 3% to about 5%, by weight.

It is within the ability of a skilled artisan to select an appropriate solvent, if desired, for the batch composition. The solvent may, for example, be used to wet the ceramic-forming powders and/or to provide a medium for the binder to dissolve, thus providing plasticity to the batch composition. In various exemplary embodiments, the at least one solvent may be aqueous, for example water and water-miscible solvents, or organic, or some combination thereof. In at least one exemplary embodiment, the solvent comprises water, for example, deionized water. According to various non-limiting embodiments, the solvent is present in the batch composition in an amount ranging from about 20% to about 50% by weight, such as about 25% to about 40%, or about 30% to about 35%, by weight.

The batch composition may optionally further comprise at least one surfactant. Non-limiting examples of surfactants that can be used in accordance with various embodiments according to the disclosure include $C_8$-$C_{22}$ fatty acids and derivatives thereof; $C_8$-$C_{22}$ fatty esters and derivatives thereof; $C_8$-$C_{22}$ fatty alcohols and derivatives thereof; and combinations thereof. In certain exemplary embodiments, the at least one surfactant may be chosen from stearic acid, lauric acid, oleic acid, linoleic acid, palmitoleic acid, ammonium lauryl sulfate, derivatives thereof, and combinations thereof. According to certain non-limiting embodiments, the at least one surfactant may be present in the batch composition in an amount ranging from about 0.5% to about 2% by weight, such as about 1% by weight.

The batch composition may optionally further comprise at least one lubricant. For example, the batch composition may comprise at least one oil lubricant chosen from light mineral oil, corn oil, high molecular weight polybutenes, polyol esters, blends of light mineral oils and wax emulsions, blends of paraffin wax in corn oil, and combinations thereof. The at least one lubricant may be present in the batch composition, in certain embodiments, in an amount ranging from about 1% to about 10% by weight, for example from about 3% to about 6%, or about 4% to about 5%, by weight.

The batch materials may be mixed to obtain a substantially homogenous batch composition using any method known in the art. For example, the at least one inorganic ceramic-forming material may be a powder which is wetted with at least one component chosen from solvents, binders, and combinations thereof. The solvent and/or binder may be added in any amount that is suitable to wet and/or plasticize the batch. The mixing and/or plasticization of the batch may take place in any suitable mixer in which the batch will be plasticized. For example, a ribbon mixer, twin-screw extruder/mixer, auger mixer, muller mixer, or double arm mixer may be used.

Methods of Making Porous Ceramic Bodies

After the batch composition is created, the batch composition is extruded to form a green body and then dried. After drying the green body may be stored for a period of time before firing to yield a porous ceramic body.

It is within the ability of one skilled in the art to determine the appropriate method and conditions for forming a porous ceramic body, such as, for example, firing conditions including equipment, temperature and duration. Such methods and conditions may depend, for example, upon the size and composition of the green body, as well as the desired properties of the porous ceramic body.

The green body may be fired at a selected temperature under a suitable atmosphere for a time dependent upon the composition, size, and geometry of the green body. For example, the green body may in some embodiments have a honeycomb geometry. In certain non-limiting embodiments, the temperature at which firing occurs may range from about 1300° C. to about 1450° C., and the firing time may range from about 1 hour to about 200 hours, for instance, from about 3 hours to about 100 hours, or from about 20 hours to about 50 hours.

The green body may also be calcined to burn out the pore former, binder, and/or surfactant, either before firing or in a temperature-rise process during firing. For instance, the binder may have a combustion temperature of about 200° C. and the pore former may have a combustion temperature ranging from about 300° C. to about 1000° C. Accordingly, the temperature at which calcination occurs may range from about 200° C. to about 1000° C., and the calcination time may range from about 10 to about 100 hours.

Screening Methods

Also disclosed herein are methods of screening green bodies for acceptable pore former formulations, which may enable cost effective and rapid evaluation, especially as compared to the traditional processes involving large scale materials blending, mixing with liquids, and extrusion through a die followed by drying and firing. As disclosed herein, shrinkage of the green body upon drying after extrusion from the die may be tracked, along with shrinkage of the green body from a dried state to a fired state. If the shrinkage upon drying is below a certain threshold amount, such as below about 5%, or, in certain embodiments, below about 4%, below about 3%, below about 2%, or below about 1%, the green body may be selected for making a porous ceramic body. In certain embodiments, if the shrinkage upon drying of the green body is less than about 5%, the green body may result in a porous ceramic body that is substantially uncracked. As used herein, the term "shrinkage" is the relative part radial or axial dimensional reduction, in percentage, as compared to the initial extruded dimensions of the body.

Screening methods have been developed to evaluate various pore formers packages. In the exemplary screening methods disclosed herein, primary responses may include shrinkage (wet-to-dry and fired) and dimensional changes due to swelling, retrogradation, and water intake (weight change). In certain embodiments, the shrinkage and dimensional changes may be measured at a given temperature and humidity. For example, in certain non-limiting embodiments, the shrinkage and dimensional changes may be measured at about 35° C. and 85% humidity and with, for example, ¼" rod samples.

Swelling, or growth, of the green body may also be measured. After the green body is dried, it may gain weight and grow as it takes on water, such as atmospheric water. The swelling correlates with an increase in weight due to absorption of water from the atmosphere by the starch particles. In fact, net weight gain may correlate with the amount of starch in the green body. Without wishing to be bound by theory, it is believed that after the growth phase, the amylose starts to leach out of the starch granule, leading to a gel layer formation surrounding the granules, which leads to high shrinkage.

The weight gain and swelling growth may be measured at various points in time to determine the weight gain and growth of the green body. In certain exemplary embodiments disclosed herein, the weight gain after about 24 hours may be less than about 5%, such as ranging from about 3% to about 5% or less than about 4%. The weight gain after the green body has fully aged may, in certain non-limiting embodiments, be less than about 5%, such as ranging from about 3% to about 5% or less than about 4%.

In certain embodiments, the growth from swelling of the green body after about 24 hours is less than about 1.0%, such as ranging from about 0.5% to about 0.8%. In certain embodiments, the growth of the green body after about 24 hours is less than about 0.8%, such as less than about 0.5% or less than about 0.4%. The growth of the green body after the green body has fully aged may, in certain non-limiting embodiments, be less than about 1%, such as ranging from about 0.4% to about 0.8%. In certain embodiments, the growth of the green body after the green body has fully aged may be less than about 0.8%, such as less than about 0.5% or less than about 0.4%. As used herein, fully aged means the point in time at which the green body will not take on substantially more atmospheric water or weight gain. In certain embodiments, a green body may be fully aged after at least about 10 days.

During the swelling/leaching of the amylose above the gelatinization point, the starch granules exhibit a change in shape (internal collapse) leading to a typical doughnut shape and formation of the so-called "granule ghost," where only the granule envelope remains. SEM pictures as shown in FIGS. 4A-C and 5A-C are evidence of this behavior during the green body drying process. During heating in the presence of humidity (e.g., during the microwave drying process) hydrogen bonds break, allowing water to enter the granule, and the granule swells and ultimately bursts releasing the amylose.

The limit on the amount of swelling that can be tolerated without cracking of the porous ceramic body can, for example, be estimated from the mechanical properties of the precursor green bodies. Cracking may, in certain embodiments, be avoided if differential strains such as those due to swelling or retrogradation processes are kept below the strain tolerance. In certain embodiments, the starch type and its concentration in the green body are chosen such that the net dimensional change in the green body through the aging process is less, for example, than about 0.5%.

The change from native to more dimensionally stable cross-linked starch may enable drying of high porosity ceramic bodies using industrial scale microwave dryers. As discussed above, there may be substantial cracking of green bodies comprising native starches. Such cracking may occur either during drying or afterwards in storage. In certain embodiments disclosed herein, however, green bodies comprising at least one crosslinked starch present in an amount of at least about 20% by weight as a super addition may be dried and stored without substantial cracking.

Unless otherwise indicated, all numbers used in the specification and claims are to be understood as being modified in all instances by the term "about," whether or not so stated. It should also be understood that the precise numerical values used in the specification and claims form additional embodiments of the disclosure. Efforts have been made to ensure the accuracy of the numerical values disclosed in the Examples. Any measured numerical value, however, can inherently contain certain errors resulting from the standard deviation found in its respective measuring technique.

As used herein the use of "the," "a," or "an" means "at least one," and should not be limited to "only one" unless explicitly indicated to the contrary.

It is to be understood that both the foregoing general description and the detailed description are exemplary and explanatory only and are not intended to be restrictive.

The accompanying drawings, which are incorporated in and constitute a part of this specification, are not intended to be restrictive, but rather illustrate embodiments of the disclosure.

Other embodiments will be apparent to those skilled in the art from consideration of the specification and practice of the disclosure.

EXAMPLES

The following examples are not intended to be limiting of the disclosure.

Example 1

Several compositions were prepared based upon a cordierite-mullite-aluminum titanate inorganics package and are shown below in Table 1. As shown in Table 1, the amount of starch added as pore formers exceeds about 30% and reaches upwards of about 35% on a dry volume basis. Table 1 also lists selected properties of interest for the tested experimental conditions, including wet-to-dry shrinkage, swelling, weight gain after 24 hours, and weight gain at full aging (e.g., after 10 days).

TABLE 1

| Pore Former | Water (%) | Drying Shrinkage (%) | Weight Gain at 24 Hours (%) | Aged Weight Gain (%) | Growth at 24 Hours (%) | Aged Growth (%) |
| --- | --- | --- | --- | --- | --- | --- |
| 6.3% F240/31.5% Native Potato/10% Graphite-Oil mixed | 22.8 | 3.44 | 4.19 | | 0.72 | 0.46 |
| KF Blend/31.5% Amioca/10% Graphite | 22.8 | 4.08 | 4.14 | | 1.31 | |
| KF Blend/31.5% Highly Crosslinked Waxy Corn/10% Graphite | 22.8 | 3.58 | 4.48 | | 0.68 | |
| KF Blend/31.5% Standard Crosslinked Waxy Corn/10% Graphite | 22.8 | 4.61 | 4.06 | | 1.46 | |

TABLE 1-continued

| Pore Former | Water (%) | Drying Shrinkage (%) | Weight Gain at 24 Hours (%) | Aged Weight Gain (%) | Growth at 24 Hours (%) | Aged Growth (%) |
|---|---|---|---|---|---|---|
| KF Blend/High Amylopectin Corn Starch | 22.8 | 4.19 | 3.82 | 5.11 | 1.61 | 1.01 |
| KF Blend/High Amylopectin Potato Starch | 22.8 | 3.30 | 4.21 | 5.10 | 1.72 | 0.90 |
| KF Blend/Hylan 5-Corn Starch with 50% Amylose | 22.8 | 5.14 | 4.35 | 5.10 | 0.92 | 0.62 |
| KF Blend/Hylan 7-Corn Starch with 70% Amylose | 22.8 | 6.54 | 4.28 | 5.00 | 0.96 | 0.81 |
| 4.5% F240/31.5% Native Potato/10% Graphite-Starch weighted separate with oil added 1% at a time for total | 23 | 2.72 | 4.04 | | 1.07 | 0.99 |
| 4.5% F240/31.5% Native Potato/10% Graphite-1% Tall Oil | 23 | 3.74 | 3.93 | | 1.26 | 1.12 |
| 4.5% F240/31.5% Native Potato/10% Graphite-2% Tall Oil | 23 | 2.50 | 4.07 | | 1.11 | 0.86 |
| 4.5% F240/31.5% Native Potato/10% Graphite-Starch weighed separate with 1% Tall Oil | 23 | 3.79 | 4.19 | | 0.83 | 0.62 |
| 6.3% F240 31.5% Emselect Very Highly Crosslinked Potato (F10153)/10% Graphite | 23 | 3.63 | 4.76 | | 0.31 | |
| 6.3% F240 31.5% Modified Sago/10% Graphite | 23 | 4.35 | 4.29 | | 0.43 | |
| 6.3% F240 31.5% Washed Very Highly Crosslinked Potato (F8684)/10% Graphite | 23 | 3.74 | 4.85 | | 0.46 | |
| 6.3% F240 31.5% Ingredion Very Highly Crosslinked Sago/10% Graphite | 23 | 3.95 | 4.47 | | 0.41 | |
| 6.3% F240/31.5% Native Potato/10% Graphite | 23.8 | 5.10 | 3.64 | 4.12 | 1.58 | 1.16 |
| 6.3% F240/31.5% Native Potato/10% Graphite-Oil mixed | 23.8 | 5.53 | 4.47 | 5.03 | 1.53 | 1.37 |
| 6.3% F240/31.5% Native Potato/10% Graphite-Oil mixed | 23.8 | 3.81 | 3.94 | | 1.37 | 1.17 |
| 6.3% F240/31.5% Sago Starch/10% Graphite | 23.8 | 4.36 | 4.34 | 4.43 | 0.34 | 0.41 |
| KF Blend/31.5% Native Potato/10% Graphite | 23.8 | 3.69 | 4.07 | 4.34 | 1.58 | 0.95 |
| KF Blend/31.5% Native Potato/10% Graphite | 23.8 | 3.77 | 2.07 | | 0.54 | 0.87 |
| KF Blend/31.5% Native Potato/10% Graphite | 23.8 | | 3.83 | 4.25 | 1.33 | 1.08 |
| KF Blend/31.5% Native Potato/10% Graphite | 23.8 | 4.05 | 5.20 | 5.56 | 0.95 | 0.76 |
| 6.3% F240 31.5% Emselect Very Highly Crosslinked Potato (F10153)/10% Graphite | 24 | 4.00 | 4.59 | | 0.77 | |
| 6.3% F240 31.5% Modified Sago/10% Graphite | 24 | 4.37 | 4.14 | | 0.60 | |
| 6.3% F240 31.5% Washed Very Highly Crosslinked Potato (F8684)/10% Graphite | 24 | 3.65 | 4.61 | | 0.67 | |

TABLE 1-continued

| Pore Former | Water (%) | Drying Shrinkage (%) | Weight Gain at 24 Hours (%) | Aged Weight Gain (%) | Growth at 24 Hours (%) | Aged Growth (%) |
|---|---|---|---|---|---|---|
| 6.3% F240/31.5% Ingredion Very Highly Crosslinked Sago/10% Graphite | 24 | 4.16 | 4.52 | | 0.49 | |
| 6.3% F240/31.5% Crosslinked Potato/10% Graphite | 24 | 4.02 | 4.25 | 4.55 | 0.47 | 0.31 |
| 6.3% F240/31.5% XL Potato/10% Graphite-Oil mixed | 24 | 5.53 | 7.31 | 7.67 | 0.41 | 0.55 |
| 31.5% Very Highly Crosslinked Low Sodium Corn/10% Graphite | 24.2 | | 4.16 | 4.41 | 0.69 | 0.63 |
| 6.3% F240/31.5% Very Highly Crosslinked Low Sodium Corn/10% Graphite | 24.2 | 4.48 | 4.39 | 4.62 | 0.88 | 0.68 |
| 6.3% F240/15.75% Native Potato/15.75% Crosslinked Pea/10% Graphite | 24.8 | 4.62 | 4.18 | 4.36 | 0.63 | 0.50 |
| 31.5% Very Highly Crosslinked Pea Starch/10% Graphite | 25.1 | | 4.31 | 4.51 | 0.52 | 0.29 |
| 6.3% F240/31.5% Bylina Pea Starch/10% Graphite | 25.1 | 5.90 | 4.08 | 4.16 | 0.76 | 0.61 |
| 6.3% F240/31.5% Bylina Pea Starch/10% Graphite-Oil mixed | 25.1 | 5.62 | 4.10 | 4.56 | 0.50 | 0.25 |
| 6.3% F240/31.5% Very Highly Crosslinked Pea Starch/10% Graphite | 25.1 | 4.03 | 4.45 | 4.69 | 0.38 | 0.34 |
| 6.3% F240/31.5% Crosslinked Pea Starch/10% Graphite | 25.1 | 5.67 | 4.00 | 4.11 | 0.77 | 0.49 |
| 6.3% F240/31.5% Crosslinked Pea/10% Graphite-Oil mixed | 25.1 | 7.00 | 3.84 | 4.71 | 1.18 | 1.03 |
| 6.3% F240/19% Native Potato/19% Crosslinked Pea | 25 | 5.00 | 5.06 | 5.24 | 0.93 | 0.63 |

Example 2

Figure 1:
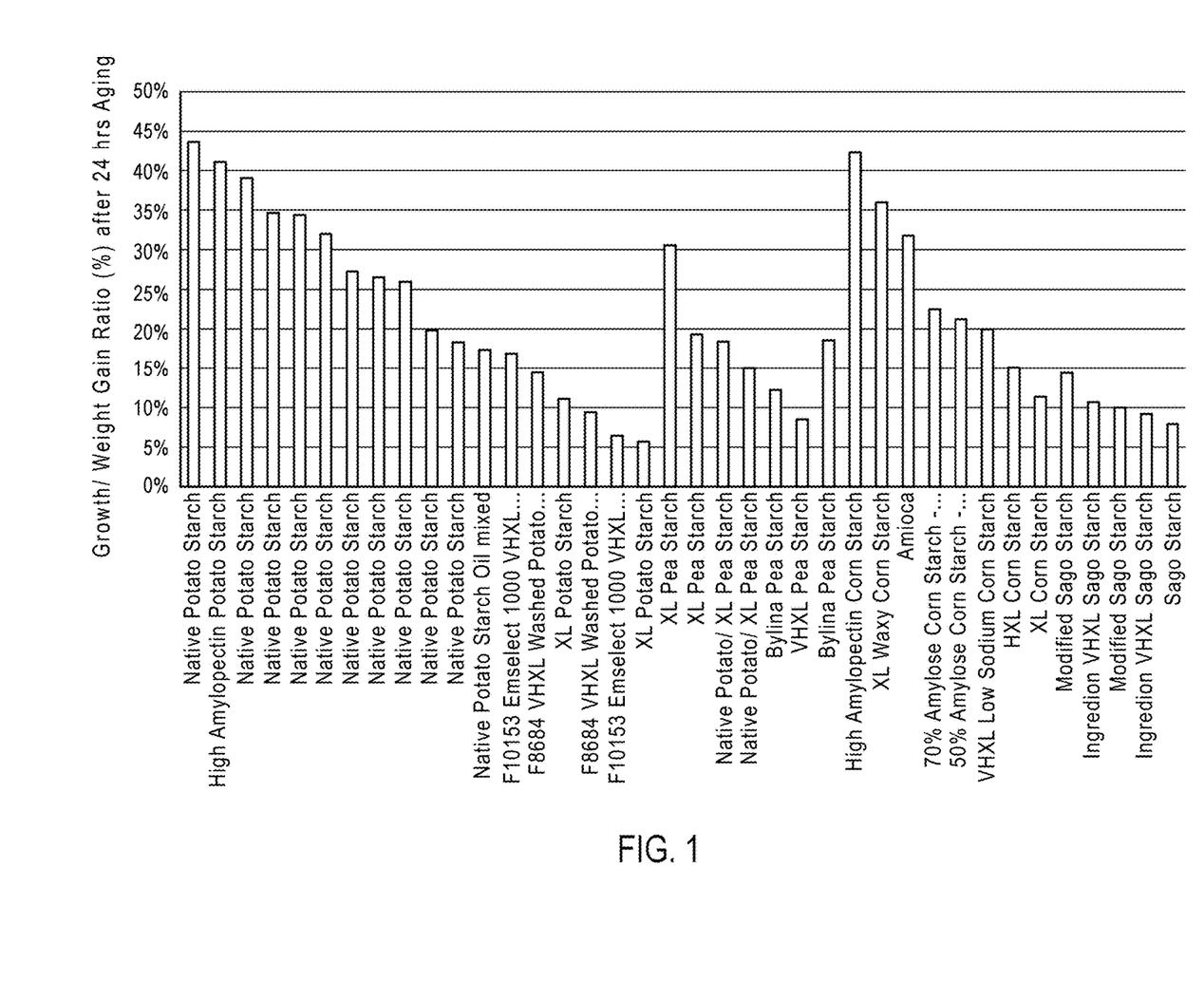
FIG. 1 is a graph of various starches showing the ratio of axial growth to weight gain after 24 hours of aging at 35° C. and 85% relative humidity, wherein XL indicates crosslinked and VHXL indicates very highly crosslinked.

The dry material growth and weight gain after 24 hours aging was measured for several batch compositions comprising various starch pore formers. FIG. 1 shows the dry material growth to weight gain ratio after 24 hours aging as a function of the type of starch pore former used. Crosslinked and heavily crosslinked starches from different sources, including potato, pea, corn, and sago, were evaluated. Also evaluated were modified starches and starches with high amylopectin or high amylose levels.

It is noted that less swelling was obtained with high amylose and crosslinked starches, which may lead to reduced stress generation during the drying, cooling, and aging of the extruded green body.

Figure 2:
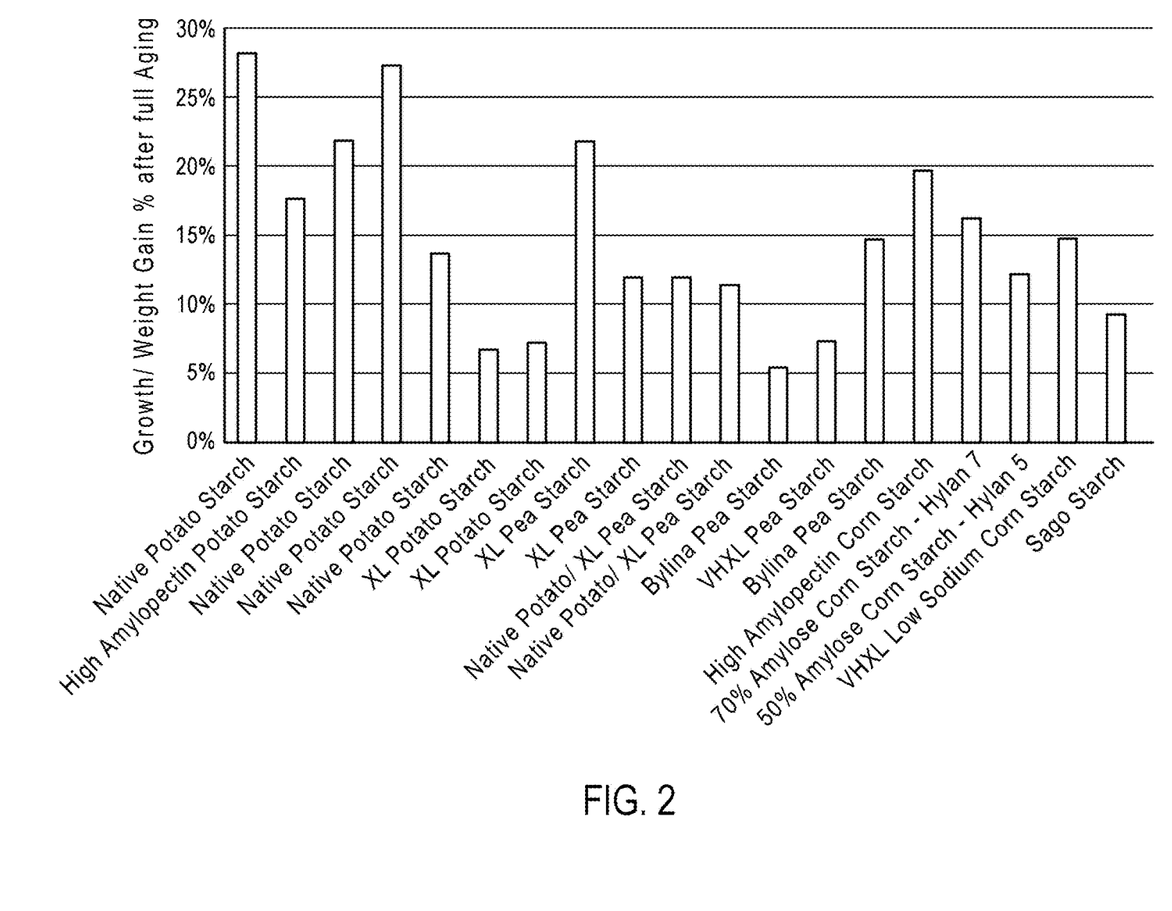
FIG. 2 is graph showing the dry material growth to weight gain ratio after full aging (e.g., after 10 days) as a function of the type of starch pore former used, including potato, pea, corn, and sago starch, wherein XL indicates crosslinked and VHXL indicates very highly crosslinked.

FIG. 2 shows the dry material growth to weight gain ratio after full aging (e.g., after 10 days) as a function of the type of starch pore former used, including potato, pea, corn, and sago starch. In FIG. 2, XL indicates crosslinked and VHXL indicates very highly crosslinked.

Example 3

Figure 3:
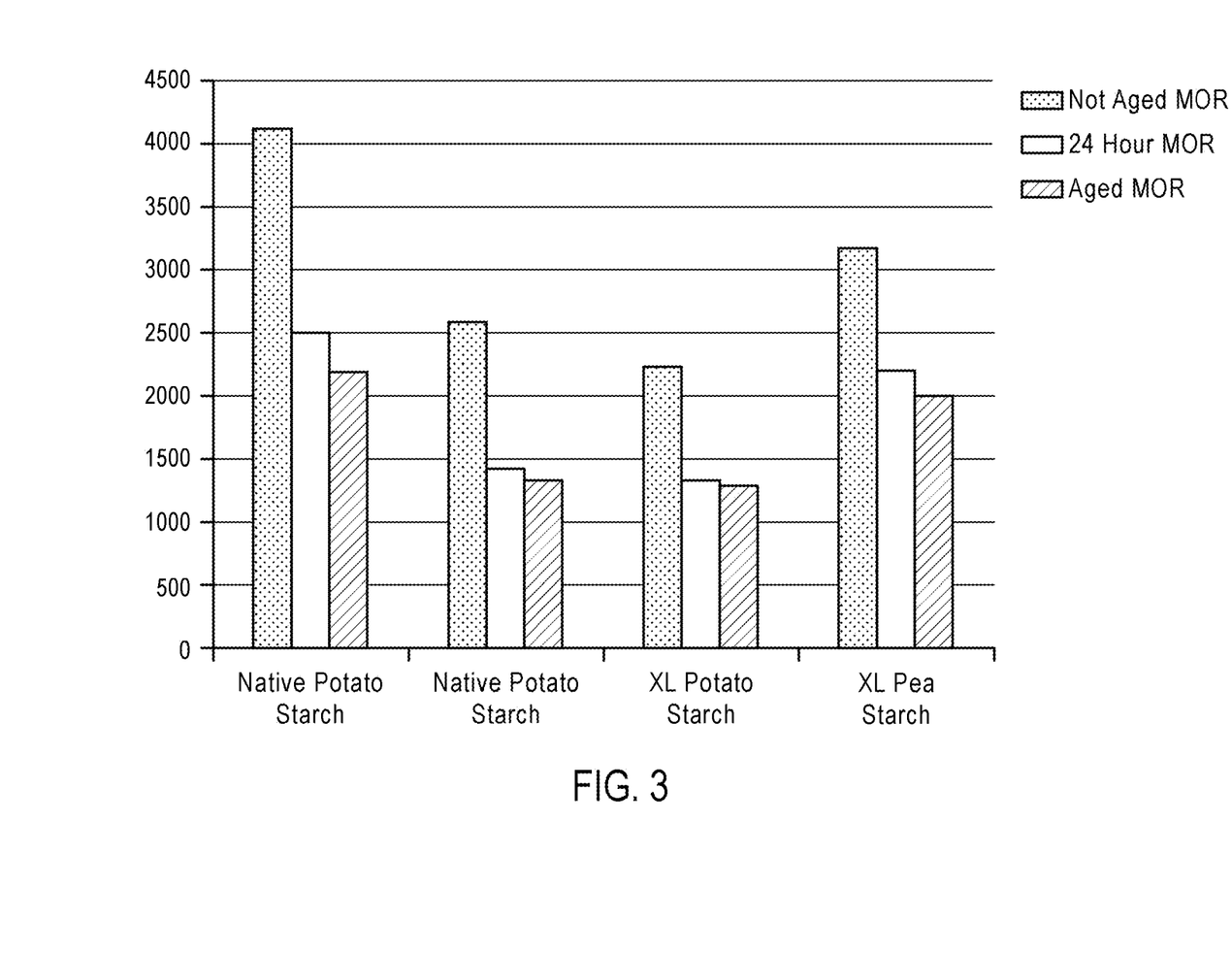
FIG. 3 is a graph showing a comparison of the modulus of rupture (MOR) for green bodies that are freshly dried, after 24 hours of aging, and after full aging, wherein the green bodies comprise different starches.

The MOR was measured for green bodies comprising various starch pore formers at three different stages of the material: fully dried, after 24 hours aging, and after full aging (e.g., 10 days). Native potato starch, crosslinked potato starch, and crosslinked pea starch were evaluated. FIG. 3 shows the MOR at the three different stages for each of the green bodies. It is noted that maximum swelling is obtained consistently after about 24 hours for each of the starch pore formers tested.

Example 4

Figure 4A:
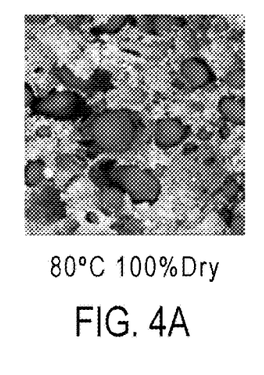
FIG. 4A shows a Scanning Electron Microscope (SEM) image of a green body comprising native potato starch granules and dried to 100% at 80° C.
Figure 4B:
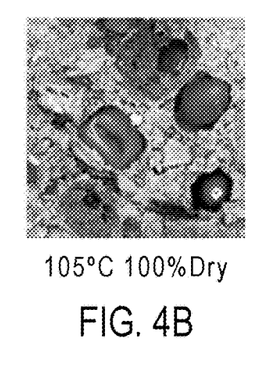
FIG. 4B shows a SEM image of a green body comprising native potato starch granules and dried to 100% at 105° C.
Figure 4C:
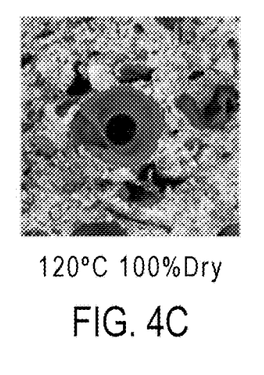
FIG. 4C shows a SEM image of a green body comprising native potato starch granules and dried to 100% at 120° C.

Scanning Electron Microscope (SEM) images were taken of fractured green bodies comprising native potato starch after drying at three temperatures representative of the microwave drying process and are shown in FIGS. 4A-C. The green bodies were dried until 100% dry at 80° C., 105° C., and 120° C., as shown in FIG. 4A, FIG. 4B, and FIG. 4C, respectively. At 120° C. oven drying temperature, it is observed that starch granules exhibit a hollow shape, are bonded to the surrounding inorganic matrix through the released amylose and are more brittle than at lower temperatures, due to retrogradation. See FIG. 4C.

At 80° C., the strain tolerance of the green body was 1664 ppm. At 105° C., the strain tolerance of the green body was 1390 ppm, and at 120° C., the strain tolerance was 1417 ppm. The sample dried at 120° C. shows more hollow and bound granules than the sample dried at 80° C. The data illustrate that the binding strength provided by the starch granules is temperature dependent.

Figure 5A:
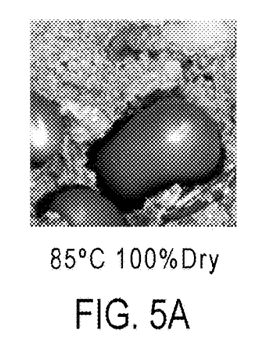
FIG. 5A shows a SEM image of a green body comprising very highly crosslinked potato starch granules and dried to 100% at 85° C.
Figure 5B:
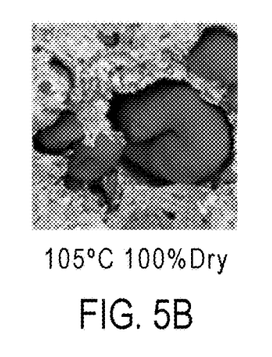
FIG. 5B shows a SEM image of a green body comprising very highly crosslinked potato starch granules and dried to 100% at 105° C.
Figure 5C:
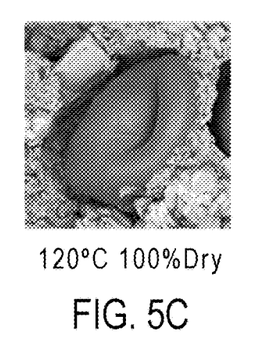
FIG. 5C shows a SEM image of a green body comprising very highly crosslinked potato starch granules and dried to 100% at 120° C.

In contrast to FIGS. 4A-C, FIGS. 5A-C shows SEM images of green bodies comprising very highly crosslinked potato starch. The green bodies were dried at three different drying temperatures of 85° C., 105° C., and 120° C., as shown in FIG. 5A, FIG. 5B, and FIG. 5C, respectively. It is noted that at 120° C., the starch granules are not bonded to the matrix, which results in less shrinkage. See FIG. 5C. It is further noted that the starch granule is still intact with swelling for oven aging at 120° C., as compared to the native potato starch shown in FIG. 4C. Very highly crosslinked starch particles are not bonded to the surrounding ceramic precursor particles, which results in less shrink and therefore eliminates cracking.

What is claimed is:

1. A method of making a porous aluminum titanate body, the method comprising:
    mixing at least one aluminum titanate-forming powder, at least one solvent, at least one binder, and at least one cross-linked starch present in an amount greater than 30% by weight as a super addition to form a batch composition;
    extruding the batch composition to form a green body;
    drying the green body completely; and
    firing the green body to form a porous aluminum titanate body,
    wherein the cross-linked starch is cross-linked to a degree sufficient to limit growth of the green body at about 35° C. and about 85% humidity to less than about 0.5% at least about 24 hours after complete drying and before the firing of the green body and to limit the shrinkage upon complete drying of the green body to less than about 4%.

2. The method of making a porous aluminum titanate body according to claim 1, wherein the porosity of the porous aluminum titanate body is greater than about 50%.

3. The method of making a porous aluminum titanate body according to claim 1, wherein the porosity of the porous aluminum titanate body ranges from about 50% to about 65%.

4. The method of making a porous aluminum titanate body according to claim 1, wherein the at least one cross-linked starch is present in the batch composition in an amount ranging from greater than 30% to about 35% by weight as a super addition.

5. The method of making a porous aluminum titanate body according to claim 1, wherein the at least one cross-linked starch is present in the batch composition in an amount ranging from greater than 30% to about 32% by weight as a super addition.

6. The method of making a porous aluminum titanate body according to claim 1, further comprising:
    after drying the green body, screening the green body to determine if the green body satisfies at least one of the following parameters:
    (i) less than about 4% shrinkage upon drying of the green body; and
    (ii) less than about 0.5% growth of the green body at least about 24 hours after complete drying.

7. The method of making a porous aluminum titanate body according to claim 1, wherein the at least one aluminum titanate-forming powder comprises an alumina source, a silica source, a titania source, and a magnesia source.

8. A method of making a porous aluminum titanate body, the method comprising:
    mixing at least one aluminum titanate-forming powder, at least one solvent, at least one binder, and at least one cross-linked starch present in an amount of about 28 to 32% by weight as a super addition to form a batch composition;
    extruding the batch composition to form a green body;
    drying the green body completely; and
    firing the green body to form a porous aluminum titanate body,
    wherein the cross-linked starch is cross-linked to a degree sufficient to limit growth of the green body at about 35° C. and about 85% humidity to less than about 0.5% at least about 24 hours after complete drying and before the firing of the green body and to limit the shrinkage upon complete drying of the green body to less than about 4%.

* * * * *

UNITED STATES PATENT AND TRADEMARK OFFICE
CERTIFICATE OF CORRECTION

PATENT NO. : 10,472,291 B2
APPLICATION NO. : 14/484509
DATED : November 12, 2019
INVENTOR(S) : Mark Alan Lewis et al.

Page 1 of 1

It is certified that error appears in the above-identified patent and that said Letters Patent is hereby corrected as shown below:

On the Title Page

On page 2, Column 2, item (56), other publications, Line 24, delete "Cermaics:" and insert -- Ceramics: --, therefor.

Signed and Sealed this
Third Day of March, 2020

Andrei Iancu
*Director of the United States Patent and Trademark Office*